US008721528B2

(12) United States Patent
Ho et al.

(10) Patent No.: US 8,721,528 B2
(45) Date of Patent: May 13, 2014

(54) ENDOSCOPE CAP

(75) Inventors: Chi-Nghia Ho, Stuttgart (DE); Gunnar Anhoeck, Reutlingen (DE); Marc O. Schurr, Tuebingen (DE)

(73) Assignee: Ovesco Endoscopy AG (DE)

( * ) Notice: Subject to any disclaimer, the term of this patent is extended or adjusted under 35 U.S.C. 154(b) by 405 days.

(21) Appl. No.: 12/997,575

(22) PCT Filed: Jun. 10, 2009

(86) PCT No.: PCT/EP2009/057210
§ 371 (c)(1),
(2), (4) Date: Apr. 26, 2011

(87) PCT Pub. No.: WO2009/150186
PCT Pub. Date: Dec. 17, 2009

(65) Prior Publication Data
US 2011/0190578 A1 Aug. 4, 2011

(30) Foreign Application Priority Data
Jun. 11, 2008 (DE) ...................... 20 2008 007 774 U

(51) Int. Cl.
*A61B 1/00* (2006.01)
*A61B 1/04* (2006.01)

(52) U.S. Cl.
USPC ............ 600/127; 600/104; 600/129; 600/149

(58) Field of Classification Search
USPC .................. 600/127, 129, 104, 121–125, 149
See application file for complete search history.

(56) References Cited

U.S. PATENT DOCUMENTS

| 5,320,630 | A |   | 6/1994  | Ahmed |         |
|-----------|---|---|---------|-------|---------|
| 6,136,009 | A | * | 10/2000 | Mears | 606/140 |
| 6,146,389 | A | * | 11/2000 | Geitz | 606/108 |
| 6,849,078 | B2|   | 2/2005  | Durgin|         |

FOREIGN PATENT DOCUMENTS

JP        2003-513737      4/2003
WO        WO 9956635 A    11/1999

OTHER PUBLICATIONS

International Search Report for PCT Application PCT/EP2009/057210, Aug. 26, 2009.
Examination Report issued by Japanese Patent Office dated Jul. 26, 2013.

* cited by examiner

*Primary Examiner* — Alireza Nia
(74) *Attorney, Agent, or Firm* — AlbertDhand LLP

(57) ABSTRACT

The present application relates to a medical gripping device (1) with a flexible shaft (2) with a front end (13) and a rear end (14) and a web (5) comprising at least one web element, wherein the web (4) is attached to the front end (3) of the shaft (2). The medical gripping device additionally has at least two branches (5, 6) which are hinged on the web (4), and at least two at least partly flexible control mechanisms (7, 151, 155, 8, 152, 156) which are at least partly arranged in the shaft (2), wherein each individual branch (5, 6) can be moved individually with respect to the web (4) by means of its individual control mechanism (7, 151, 155, 8, 152, 156). Furthermore, the medical gripping device has a grip (150) at the rear end (14) of the flexible shaft (2), by mans of which grip the medical gripping device (1) can be held and actuated.

7 Claims, 5 Drawing Sheets

ENDOSCOPE CAP

The present invention relates to an endoscope cap for positioning tissue clips preferably in hollow organs of a human or animal body.

From the state of the art, for instance according to U.S. Pat. No. 6,849,078 B2, a tissue clip of this species is generally known as regards its basic design. For a better comprehension, this tissue clip is described hereinafter in detail with reference to FIG. 1.

Accordingly, such clip 100 consists of a mouth-type clamping means having two toothed jaws 110, 120 adapted to be opened and shut via two lateral hinges 130 or by flexible moldings. The hinges 130 or the flexible moldings are preferably formed of spring-elastic straps which during opening the jaws 110, 120 store spring energy which results in a snapping of the jaws 110, 120 at a predetermined clamping force when the jaws 110, 120 are released, i.e. when the hinges 130 or the flexible moldings are actuated.

In detail, each clip 100 is punched in one piece out of a spring steel sheet by working a ring having a partially different ring width out of the spring steel sheet. Two diametrically opposed ring portions having a large ring width constitute the two jaws 110, 120, whereas the two ring portions disposed there between having a narrow ring width form the hinges 130 or the flexible moldings. The jaws 110, 120 are formed by arching the ring portions having a large ring width in a curved shape, wherein the two ring portions having a narrow ring width are twisted about their longitudinal axis by approx. 180° in order to form the hinges. This special shaping of the punched out spring steel sheet creates the shape of a type of shark mouth having two rows of teeth moving toward each other which are formed by punching out the ring portions having a large ring width.

The functioning of the afore-described medical tissue clip 100 can be described as follows:

In general, an endoscopic implantation of a medical device in total constitutes the most tolerable process for the patient. In this case the medical device must be fixed from the inside of a hollow organ to the latter. For this purpose, a number of the afore-described tissue cleats, clips or anchors are inserted into the hollow organ by means of an endoscope and are positioned at predetermined positions at the inner face of the organ. To this end, the respective clip or anchor is brought close to the organ tissue and the biasing spring is released for snapping of the clip or clamping of the anchor. The latter then clamps or holds a tissue fold between its jaws or its hooks or needles at a predetermined clamping or expanding force, wherein the teeth, hooks, needles or jags of each jaw cut into the tissue and preferably penetrate the same. In this way the clips or anchors are anchored to the inner face of the organ at predetermined spaces and thus form introducing points into the organ tissue for a tensile force.

Figure 1:
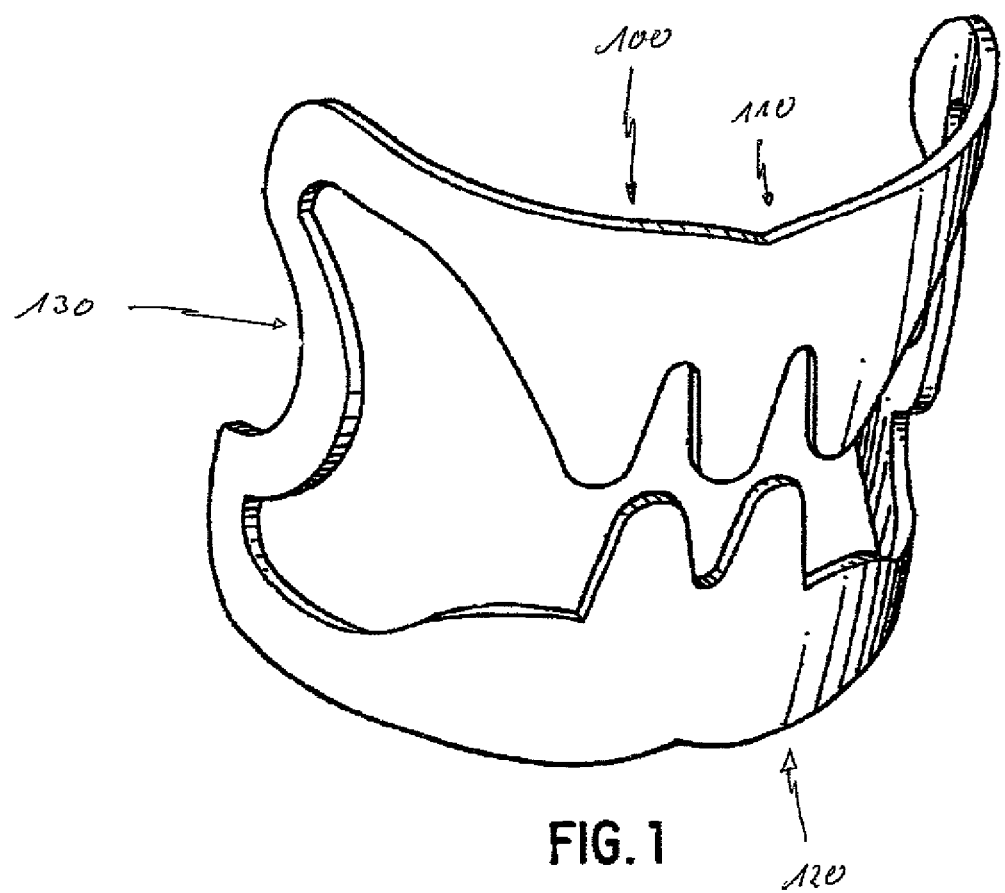

The endoscope not shown in detail in FIG. 1 usually is equipped with an endoscope head or an endoscope cap which includes, apart from the functions generally required for an endoscope such as lighting, optical system and rinsing means, if necessary, in addition a holding and withdrawing means for the tissue clip. This holding and withdrawing means substantially consists of an expanding sleeve as well as a slide operable manually or by remote control which is movable in the longitudinal direction of the endoscope. The expanding sleeve is configured such that the already opened tissue clip can be attached to the sleeve in such manner that the clip can be prevented from slipping backwards while being inserted into the hollow organ. For this purpose, the slide is positioned axially behind the clip and serves so-to-speak as an axial stop for the clip.

As soon as the clip is to be positioned at a particular site, the slide is moved axially forward and in so doing strips off the clip over the expanding sleeve. Accordingly, the clip is actuated, i.e. the biasing mechanism within the clip described before by way of FIG. 1 is released when the latter is stripped off the expanding sleeve and the two jaws of the tissue clip snap to close while clamping the tissue provided there between.

In endoscopes of this species the endoscope diameter is of salient importance to the functioning thereof. In this respect, the basic problem is that the endoscope cap including all necessary functions has a large volume and therefore the range of application of such endoscope is restricted.

In view of this problem, it is the object of the present invention to provide an endoscope cap for positioning an already known tissue clip which has an as small size as possible.

This object is achieved by an endoscope cap comprising the technical features according to claim 1.

Consequently, the core of the invention consists in forming a front groove opened to both sides (or ends thereof) in circumferential direction at the outer circumference of the expanding sleeve (forming a tongue—like axial protection) for receiving a tissue clip through which a thread or tissue is pulled in the radial direction. The thread is fixed at one end at the endoscope or at the endoscope cap and is movably guided along the endoscope at the other end so that when pushing the tissue clip into the groove the thread can be entrained by the same. If subsequently the thread is pulled, it tends to shrink inside the front groove, wherein the tissue clip is pushed out of the groove again by the thread.

Consequently, a function-related constructional division of the holding and withdrawing means is achieved in this way, viz. into arranging the front groove/slit forming an axial stop as well as into arranging a thread simulating a slide which is separate hereto. This constructional division of the holding and withdrawing means permits to design especially the withdrawing means as a highly flexible thread or cable which requires a small space only and still is adapted to exert sufficiently high displacing forces especially when using the afore-described block-and-tackle mechanism upon the clip.

Further advantageous configurations of the invention are the subject matter of the subclaims.

Figure 2:
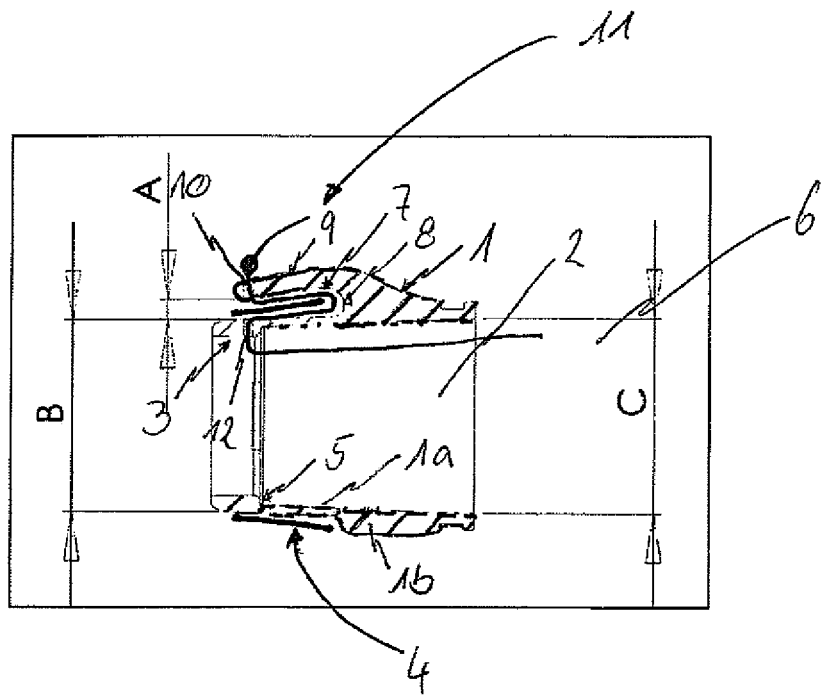
Figure 3:
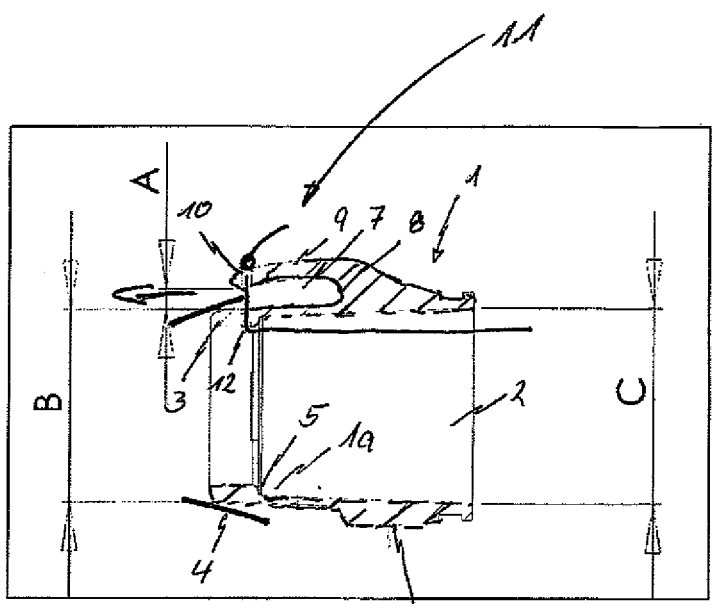
Figure 4:
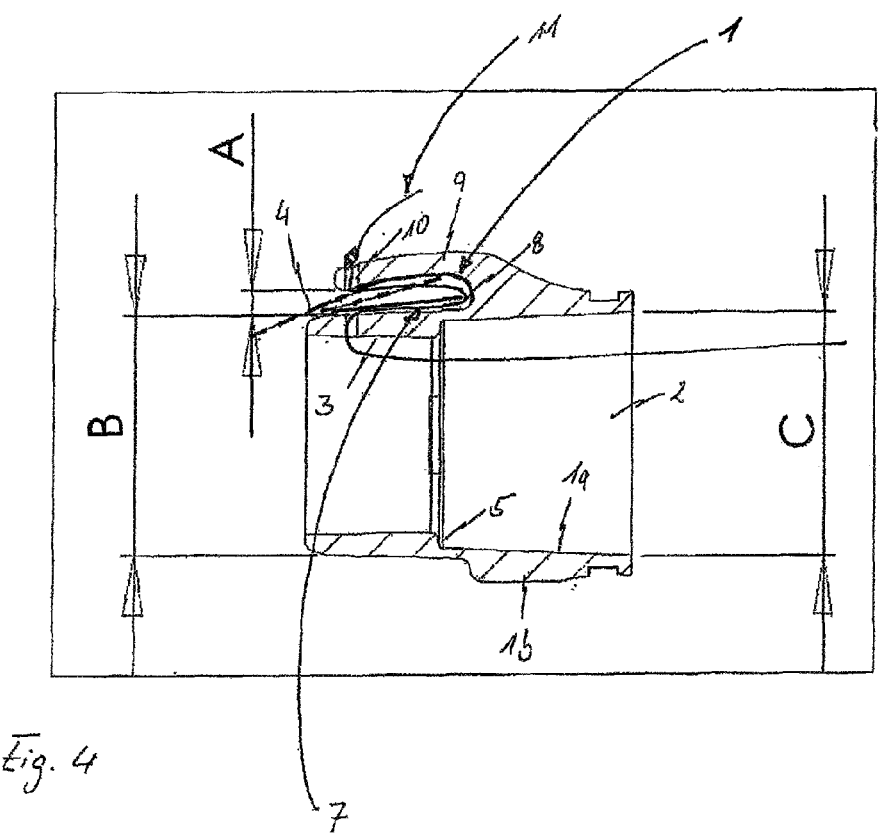
Figure 5A:
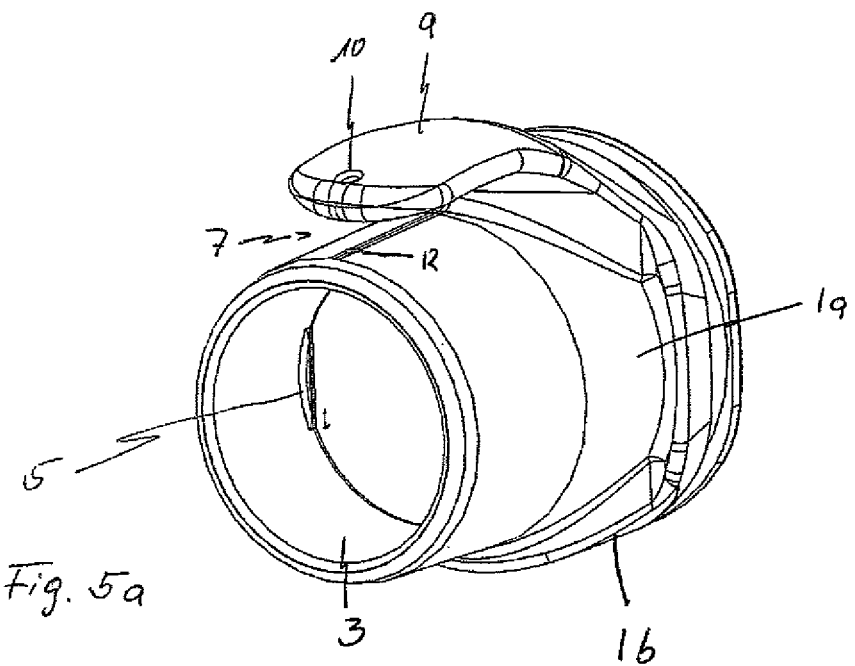
Figure 5B:
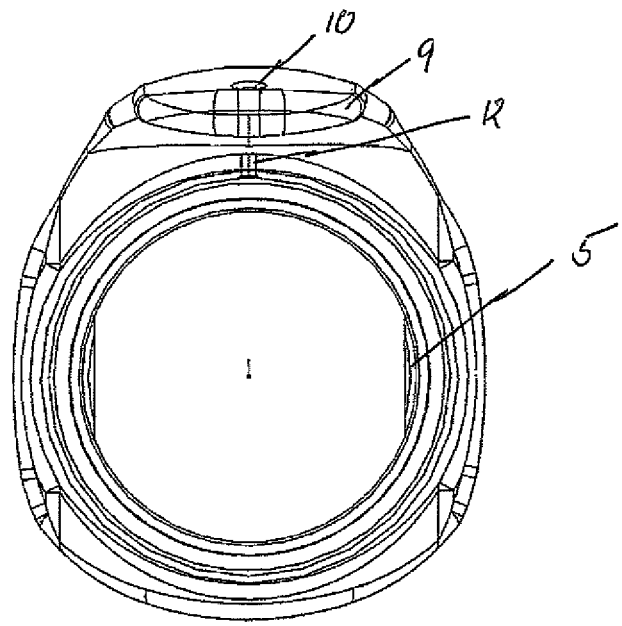
Figure 6C:
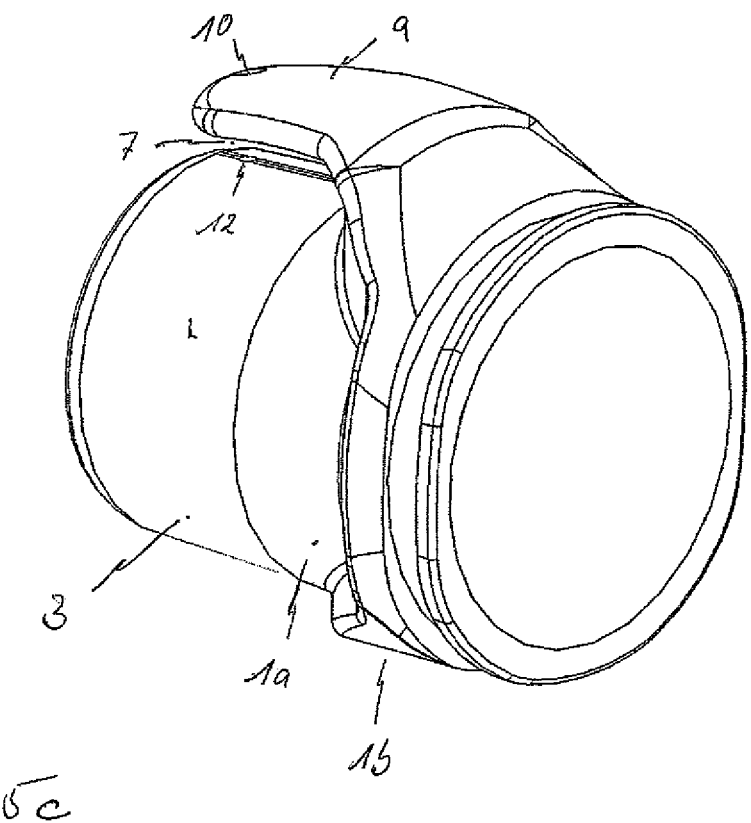

Hereinafter the invention is explained in detail by way of a preferred embodiment with reference to the accompanying drawings, in which FIG. 1 shows the exemplary design of a tissue clip as it is known already from the state of the art and as it is equally employed in the present invention, FIG. 2 illustrates the longitudinal section of an endoscope cap according to the invention including an attached tissue clip according to FIG. 1 in schematic representation, FIG. 3 illustrates the longitudinal section of FIG. 2 including actuated holding and withdrawing means according to the invention, FIG. 4 shows the stepwise functional representation of the holding and withdrawing means according to the invention during the actuating phase and FIG. 5a-5c show a variant for providing a front groove guiding the clip at the circumferential cap wall.

In FIG. 2 an endoscope cap 1 according to a preferred embodiment of the invention at the distal end of an endoscope or trocar which can be inserted in a hollow organ of a human or animal body.

The endoscope cap 1 according to the invention includes a slip-on portion 1a in the mounted state surrounding a distal endoscope head 2 which is optionally equipped with endoscope-specific functions, for instance lighting, optical means, rinsing means, working channel mouth etc., which are individually operable by a handle provided at the proximal end of the endoscope. The endoscope cap 1 is formed at an axial distance from the slip-on portion 1a at the sheath side to or with an expanding sleeve 3 onto which a tissue clip 4 can be slipped, as it was described in detail in the foregoing by way of FIG. 1. This expanding sleeve 3 axially protrudes from the distal end face of the endoscope head 2 and thus forms a free annular portion radially outwardly rounded at its front edge. For an exact axial positioning of the endoscope cap 1 it has a radially inner circumferential edge 5 which is pressed to the end face of the endoscope head 2 and thus prevents the cap 1 from being displaced along the endoscope in the direction of the proximal end thereof.

In the present preferred embodiment the endoscope cap 1 at the same time also constitutes the housing for the endoscope head 2 and consequently is fixedly and tightly connected as a part of the endoscope to an endoscope shaft 6 which is merely indicated in FIG. 2. As an alternative to that, the endoscope cap 1 having the same constructional design can also be manufactured as a component separate from the endoscope head 2, however, which can be pushed onto or attached to an already existing housing of the endoscope head 2 having the corresponding functions and therefore is suited as a retrofit kit of commercial endoscopes.

The endoscope cap 1 according to the invention in each case includes a front groove 7 introduced from the end face in the sheath-side cap wall, the front groove opening as a pitch circle or sickle-shaped slit at the distal end face of the endoscope head 2 or the cap 1 and the groove bottom thereof forming a stop 8 at an axially rear position, preferably approximately at an axially central portion of the endoscope head 2 (in the axially central area of the slip-on portion 1a). The radius of the front groove 7 is selected to be larger, however, than the radius of the endoscope cap 1 so that when forming the front groove 7 two slits appropriately spaced in circumferential direction are imparted to the cap wall. By forming said front groove slits the cap sheath wall in this area is thus longitudinally split, thereby a type of tab or tongue 9 defining the radially outer groove wall being formed at the outside of the cap wall.

According to FIGS. 5a-5c, another variant of providing a front groove according to the above definition is represented by the additional arrangement of a tab or tongue 9 preferably curved in axial direction whose root is formed integrally with the cap 1 in the area of the slip-on portion 1a and which extends, while forming the groove 7, at a radial distance from the cap sheath wall axially in the direction of the expanding sleeve 3. Consequently, in this case the sheath wall is not split (as described in the foregoing), but an additional component in the form of the tab 9 is guided over the sheath wall of the cap 1. Said tab 9 can be dimensioned to be so small that it remains straight (without radius) in cross-section (cf. especially FIG. 5b), i.e. it need not necessarily follow the cap circumference. Moreover, the shape of the ground plan of the tab can most largely have any design, i.e. it can be thickened and/or widened in the direction of the root according to FIG. 5c so as to obtain higher stiffness. Also the tab root itself can be freely dimensioned and designed under static aspects to obtain as high stiffness as possible.

Irrespective of the manufacturing variant according to which the tab 9 is finally formed, in accordance with the invention it extends from the ground bottom constituting the stop 8 in the direction of the distal end face of the endoscope head 2 or the cap 1, wherein the rounded free front edge thereof is slightly axially reset vis-à-vis the distal front edge of the expanding sleeve 3.

As one can recognize especially from FIGS. 2, 3 and 5, the front groove 7 does not extend exactly in parallel to the central axis of the endoscope or cap but is inclined in the direction of the distal end face toward the central axis. Moreover, the groove 7 is not straight but the groove walls thereof, at least the outer groove wall, are slightly curved in the axial direction such that the groove 7 bulges radially outwardly at its axial central portion.

At an axial front end portion of the tab 9, the same is provided with a radial outer through bore 10 through which a thread 11 or tissue is guided from the inside of the groove in the direction of the outside of the cap 1 and is fixed there. Preferably, for this purpose the one thread end is knotted to the outside of the cap wall so that the thread 11 is prevented from being withdrawn through the outer through bore 10. Furthermore, at a position substantially radially opposed to the afore-mentioned through bore 10, i.e. in the area of the axially protruding expanding sleeve 3, the endoscope cap 1 is provided with a radial inner through bore 12 through which the thread 11 is guided from the interior of the groove to the inside.

As one can infer especially from FIG. 3, the inner through bore 12 is provided axially directly ahead of the distal end face of the endoscope head 2 so that the thread 11 coming from the inner through bore 12 can be threaded into a function channel opening at the end face of the head or the working channel of the endoscope without having to overcome a long free distance.

Hereinafter, the operating mode of the endoscope cap according to the invention having the holding and withdrawing function is described in detail especially with reference to FIG. 4.

In order to move a tissue clip, for instance according to FIG. 1, 4 to its predetermined position, it has first of all to be pulled onto the expanding sleeve 3 of the endoscope cap 1. To this end, the lower and upper jaws of the tissue clip 4 are manually folded up so that the clip 4 can be attached to the rounded front edge of the expanding sleeve 3 and can be pushed over the same. The rear edge of the tissue clip 4 penetrates the front groove 7 of the endoscope cap 1 and pulls the thread 11 out of the function or working channel of the endoscope shaft 6.

Finally the displacing movement of the clip 4 comes to a standstill when it contacts the groove bottom 8, wherein the clip 4 and the entrained thread 11 adopt the position shown in FIG. 2. That is to say, at this position the clip 4 is completely pulled onto the endoscope cap 1 and in this way can be introduced via the endoscope 2 into a hollow organ. The thread 11 encompasses the rear edge of the clip 4 and thus is given a U-shape viewed in the longitudinal direction of the thread.

If the clip 4 is to be stripped off, the thread 11 guided through the shaft passage to the proximal end of the endoscope is pulled, wherein the thread portion crossing the front groove 7 in the radial direction shrinks. As the thread 11 is fixed in the outer through bore 10, it exerts a force in axial direction on the clip 4 at an appropriate ratio according to the block-and-tackle principle, thereby the clip 4 being displaced in the direction of the distal end of the endoscope cap 1. The outer rounding of the front expanding sleeve edge and the smooth, viz. arched shaping of the front groove 7 facilitate sliding of the clip 4 over the front edge of the expanding sleeve 3 and further reduce the maximum displacing force to be applied via the thread 11. As soon as the rear edge of the clip 4 has left the front groove 7 and therefore can no longer be held by the tab 9, the biasing force stored in the clip 4 causes the clip 4 to come off the expanding sleeve 3. In this way the withdrawing operation is completed and the endoscope can be removed from the hollow organ.

The invention claimed is:

1. An endoscope cap comprising:
   a holding and withdrawing means for mounting a slipped-on tissue clip adapted to be slipped onto an expanding sleeve of the endoscope cap, the holding and withdrawing means comprising:
   a tab fixed to the endoscope cap, wherein the tab extends at a radial distance from a cap sheath wall of the endoscope cap longitudinally with respect to the endoscope cap,
   a front groove formed between the tab and the cap sheath wall, the front groove including a front groove opening at a front edge of the expanding sleeve, and
   a withdrawing thread or fabric fixed to the tab, the withdrawing thread or fabric radially penetrating the front groove at an axial front cap portion distally with respect to the slipped-on tissue clip, the withdrawing thread or fabric being proximally guided around the slipped-on tissue clip in a loop and movably introduced into an endoscope channel for operating the withdrawing thread or fabric at a radial inner side of the endoscope cap distally with respect to the slipped-on tissue clip.

2. The endoscope cap according to claim 1, wherein the tab is provided at its free front end with an outer radial bore through which the thread or fabric is guided and anchored to the tab, wherein radially opposed thereto at the expanding sleeve, an inner radial through bore is formed through which the thread is movably guided after crossing the front groove.

3. The endoscope cap according to claim 1, wherein the endoscope cap includes a slip-on portion adapted to be slipped or screwed onto the distal end of an endoscope shaft to which the expanding sleeve is integrally connected at an axial distance.

4. The endoscope cap according to claim 3, wherein the thread or fabric leaves the front groove axially ahead of the slip-on portion.

5. The endoscope cap according to claim 4, further comprising a radially inner circumferential shoulder configured to act as an axial restriction of the slip-on portion and as an axial stop for a plugged-in or screwed-in endoscope shaft.

6. The endoscope cap according to claim 1, wherein the front groove is inclined in the direction of the front edge of the cap toward a central axis of the cap and/or is arched radially outwardly in the longitudinal direction of the cap.

7. The endoscope cap according to claim 1, further comprising an outer radial thickening or bead at an outside of the cap sheath wall which extends backwards in the axial direction starting from an axial area of a groove bottom of the front groove and is substantially guided around an entire circumference of the cap.

* * * * *